(12) United States Patent
Ozsecen

(10) Patent No.: US 12,741,096 B2
(45) Date of Patent: Sep. 22, 2026

(54) CURVED RESERVOIR FOR MEDICAL INJECTOR

(71) Applicant: Becton, Dickinson and Company, Franklin Lakes, NJ (US)

(72) Inventor: Muzaffer Yalgin Ozsecen, Groton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 937 days.

(21) Appl. No.: 17/958,900

(22) Filed: Oct. 3, 2022

(65) Prior Publication Data

US 2023/0115856 A1 Apr. 13, 2023

Related U.S. Application Data

(60) Provisional application No. 63/253,321, filed on Oct. 7, 2021.

(51) Int. Cl.
*A61M 5/24* (2006.01)
*A61M 5/142* (2006.01)

(52) U.S. Cl.
CPC .............. *A61M 5/24* (2013.01); *A61M 5/142* (2013.01)

(58) Field of Classification Search
CPC .... A61M 5/14248; A61M 5/24; A61M 5/142; A61M 5/1454; A61M 2005/31518
See application file for complete search history.

(56) References Cited

U.S. PATENT DOCUMENTS

| | | | | |
|---|---|---|---|---|
| 4,525,164 | A * | 6/1985 | Loeb | A61M 5/148 222/326 |
| 10,130,756 | B2 | 11/2018 | Hadváry et al. | |
| 2004/0087904 | A1 * | 5/2004 | Langley | A61M 5/31553 604/131 |
| 2005/0065466 | A1 | 3/2005 | Vedrine | |
| 2008/0009823 | A1 | 1/2008 | McKay | |
| 2008/0051709 | A1 | 2/2008 | Mounce et al. | |
| 2016/0263312 | A1 * | 9/2016 | Junod | A61M 5/1452 |
| 2021/0154410 | A1 * | 5/2021 | Olivas | A61M 5/1454 |

FOREIGN PATENT DOCUMENTS

| | | |
|---|---|---|
| KR | 101615745 B1 | 4/2016 |

* cited by examiner

*Primary Examiner* — Bhisma Mehta
*Assistant Examiner* — Marissa Taylor
(74) *Attorney, Agent, or Firm* — The Webb Law Firm

(57) ABSTRACT

A reservoir and drive assembly for a medical injector including a curved barrel having a first end and a second end positioned opposite the first end, with the curved barrel defining an interior space configured to receive a fluid, a stopper received within the interior space, with the stopper configured to move within the curved barrel to dispense fluid from the curved barrel, a curved plunger rod having a first end and a second end positioned opposite from the first end, with the curved plunger connected to the stopper, and at least one gear configured to drive the curved plunger rod and move the stopper within the curved barrel.

10 Claims, 6 Drawing Sheets

54
52
56
90

80
84
62
54
98
52
56
94

96
92
80

98
54
52
56
60
58
100
80

54
98
52
56
106
100
60
80
58

54
98
52
56
60
106
100
80
104

54
52
56

80
84
108

CURVED RESERVOIR FOR MEDICAL INJECTOR

CROSS-REFERENCE TO RELATED APPLICATION

The present application claims priority to U.S. Provisional Application Ser. No. 63/253,321, entitled "Curved Reservoir for Medical Injector", filed Oct. 7, 2021, the entire disclosure of which is hereby incorporated by reference in its' entirety.

BACKGROUND OF THE INVENTION

Field of the Invention

The present disclosure relates to a curved reservoir for a medical injector.

Description of Related Art

Wearable medical devices, such as automatic injectors, have the benefit of providing therapy to the patient at a location remote from a clinical facility and/or while being worn discretely under the patient's clothing. The wearable medical device can be applied to the patient's skin and configured to automatically deliver a dose of a pharmaceutical composition within a predetermined time period after applying the wearable medical device to the patient's skin, such as after a 27 hour delay. After the device delivers the pharmaceutical composition to the patient, the patient may subsequently remove and dispose of the device. Wearable medical devices can use cylindrical barrel-style reservoirs. The use of barrel-style reservoirs can limit the volume and/or length of the reservoir due to the effect of the reservoir length on the overall package size of the wearable medical device.

SUMMARY OF THE INVENTION

In one aspect or embodiment, a reservoir and drive assembly for a medical injector includes a curved barrel having a first end and a second end positioned opposite the first end, with the curved barrel defining an interior space configured to receive a fluid, a stopper received within the interior space, with the stopper configured to move within the curved barrel to dispense fluid from the curved barrel, a curved plunger rod having a first end and a second end positioned opposite from the first end, with the curved plunger rod connected to the stopper, and at least one actuator inducing movement of the stopper within the curved barrel, such as a gear configured to drive the curved plunger rod and move the stopper within the curved barrel.

The curved plunger rod and at least a portion of the stopper may be formed integrally. The curved barrel may be curved along an entire length extending from the first end of the curved barrel to the second end of the curved barrel. The curved plunger rod may be curved along an entire length extending from the first end of the curved plunger rod to the second end of the curved plunger rod.

The assembly may further include an electric motor configured to drive the at least one gear. The at least one gear may include a worm gear, a pinion gear, and a planetary gear set. The electric motor may include a drive shaft, with the worm gear secured to the drive shaft and the pinion gear engaged with the worm gear and the planetary gear set. A drive arm may be connected to the planetary gear set, with the drive arm connected to the curved plunger rod.

The assembly may further include a printed circuit board assembly, with the printed circuit board assembly being C-shaped. The curved barrel may have a circular cross-section along a direction extending perpendicular to a curved central axis extending from the first end to the second end of the curved barrel.

In a further aspect or embodiment, a medical injector includes the reservoir and drive assembly of any of the aspects or embodiments discussed above, a power source, and a cannula configured to be inserted into a skin of a patient.

In a further aspect or embodiment, a reservoir and drive assembly for a medical injector includes a curved barrel having a first end and a second end positioned opposite the first end, with the curved barrel defining an interior space configured to receive a fluid, a stopper received within the interior space, with the stopper configured to move within the curved barrel to dispense fluid from the curved barrel, a curved plunger rod having a first end and a second end positioned opposite from the first end, with the curved plunger rod connected to the stopper, and a drive assembly including a rotational spring configured to drive the curved plunger rod and move the stopper within the curved barrel.

In a further aspect or embodiment, a reservoir and drive assembly for a medical injector includes a curved barrel having a first end and a second end positioned opposite the first end, with the curved barrel defining an interior space configured to receive a fluid, a stopper received within the interior space, with the stopper configured to move within the curved barrel to dispense fluid from the curved barrel, a curved plunger rod having a first end and a second end positioned opposite from the first end, with the curved plunger rod connected to the stopper, and a drive assembly including an electric motor directly connected to the curved plunger rod via a drive arm, with the electric motor configured to drive the curved plunger rod and move the stopper within the curved barrel.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". By "about" is meant a range of plus or minus ten percent of the stated value. As used in the specification and the claims, the singular form of "a", "an", and "the" include plural referents unless the context clearly dictates otherwise. The terms "first", "second", and the like are not intended to refer to any particular order or chronology, but instead refer to different conditions, properties, or elements. By "at least" is meant "greater than or equal to".

Figure 1:
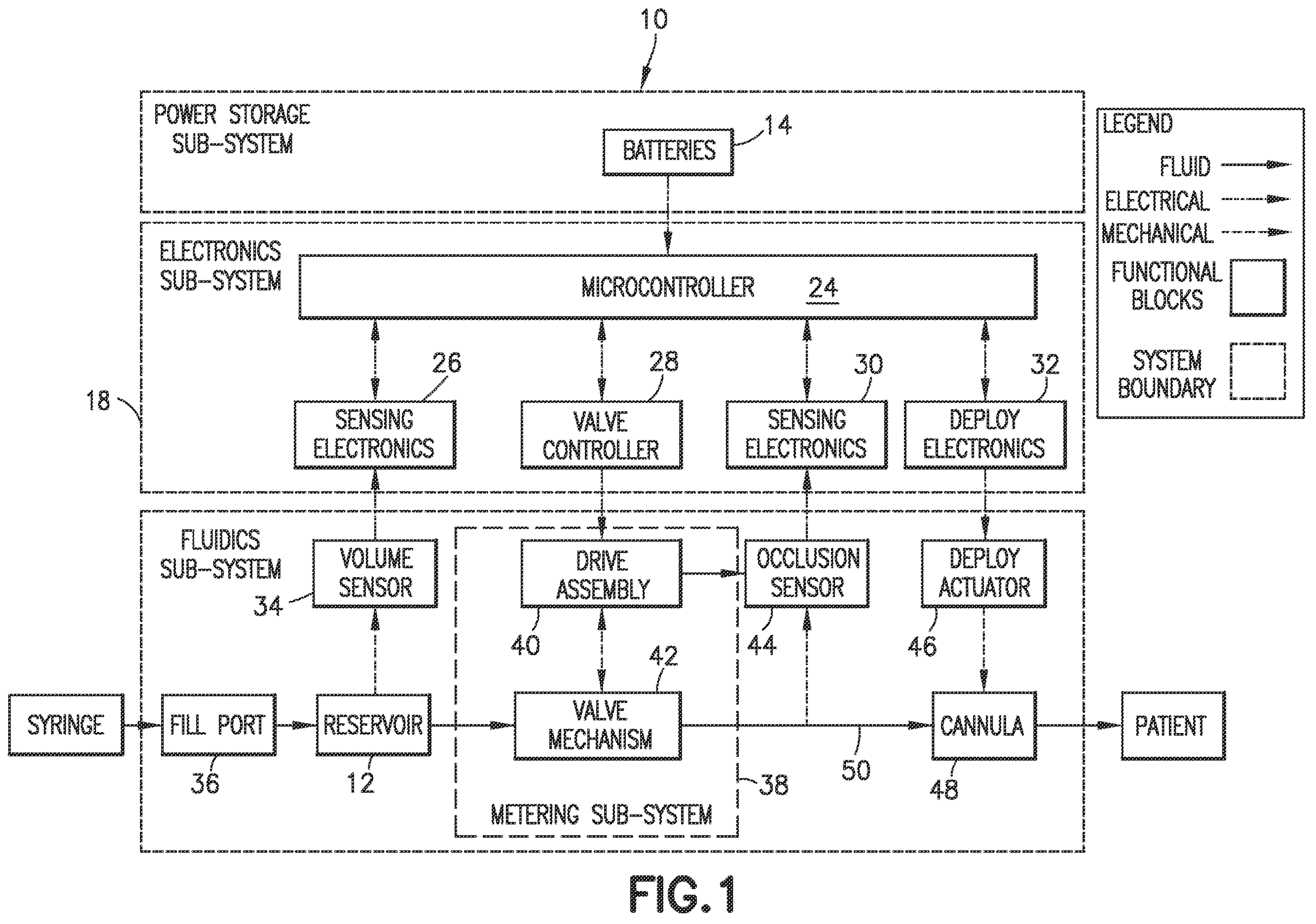
FIG. 1 is a schematic view of a drug delivery device according to one aspect or embodiment of the present application.

Referring to FIG. 1, a medical injector 10 includes a reservoir 12, a power source 14, and control electronics 18. In one aspect or embodiment, the medical injector 10 is a wearable automatic injector configured to deliver a dose of medicament. The medical injector 10 may be mounted onto the skin of a patient and triggered to inject a medicament from the reservoir 12 into the patient. The medical injector 10 may be pre-filled with the medicament or pharmaceutical composition, or it may be filled with the medicament or pharmaceutical composition by the patient or medical professional prior to use. In one aspect or embodiment, the medical injector 10 is utilized for an infusion of a medicament.

The medical injector 10 is configured to deliver a dose of a pharmaceutical composition, e.g., any desired medicament, into the patient's body by a subcutaneous injection at a controlled injection rate. Exemplary time durations for the delivery achieved by the medical injector 10 may range from about 5 minutes to about 60 minutes, but are not limited to this exemplary range. Exemplary volumes of the pharmaceutical composition delivered by the medical injector 10 may range from about 0.1 milliliters to about 10 milliliters, but are not limited to this exemplary range. The volume of the pharmaceutical composition delivered to the patient may be adjusted.

In one aspect or embodiment, the power source 14 is a DC power source including one or more batteries. In one aspect or embodiment, the control electronics 18 include a microcontroller 24, sensing electronics 26, a valve controller 28, sensing electronics 30, and deployments electronics 32, which control the actuation of the medical injector 10. In one aspect or embodiment, the medical injector 10 includes a fluidics sub-system that includes the reservoir 12, volume sensor 34 for the reservoir 12, a reservoir fill port 36, and a metering system 38 including drive assembly 40 and valve mechanism 42. The fluidic sub-system may further include an occlusion sensor 44, a deploy actuator 46, a cannula 48 for insertion into a patient's skin, and a fluid line 50 in fluid communication with the reservoir 12 and the cannula 48. In an alternative aspect or embodiment, the occlusion sensor is a system for measuring motor current. In one aspect or embodiment, an insertion mechanism (not shown) is configured to move the cannula 48 from a retracted position positioned entirely within the device 10 to an extended position where the cannula 48 extends outside of the device 10.

Figure 2:
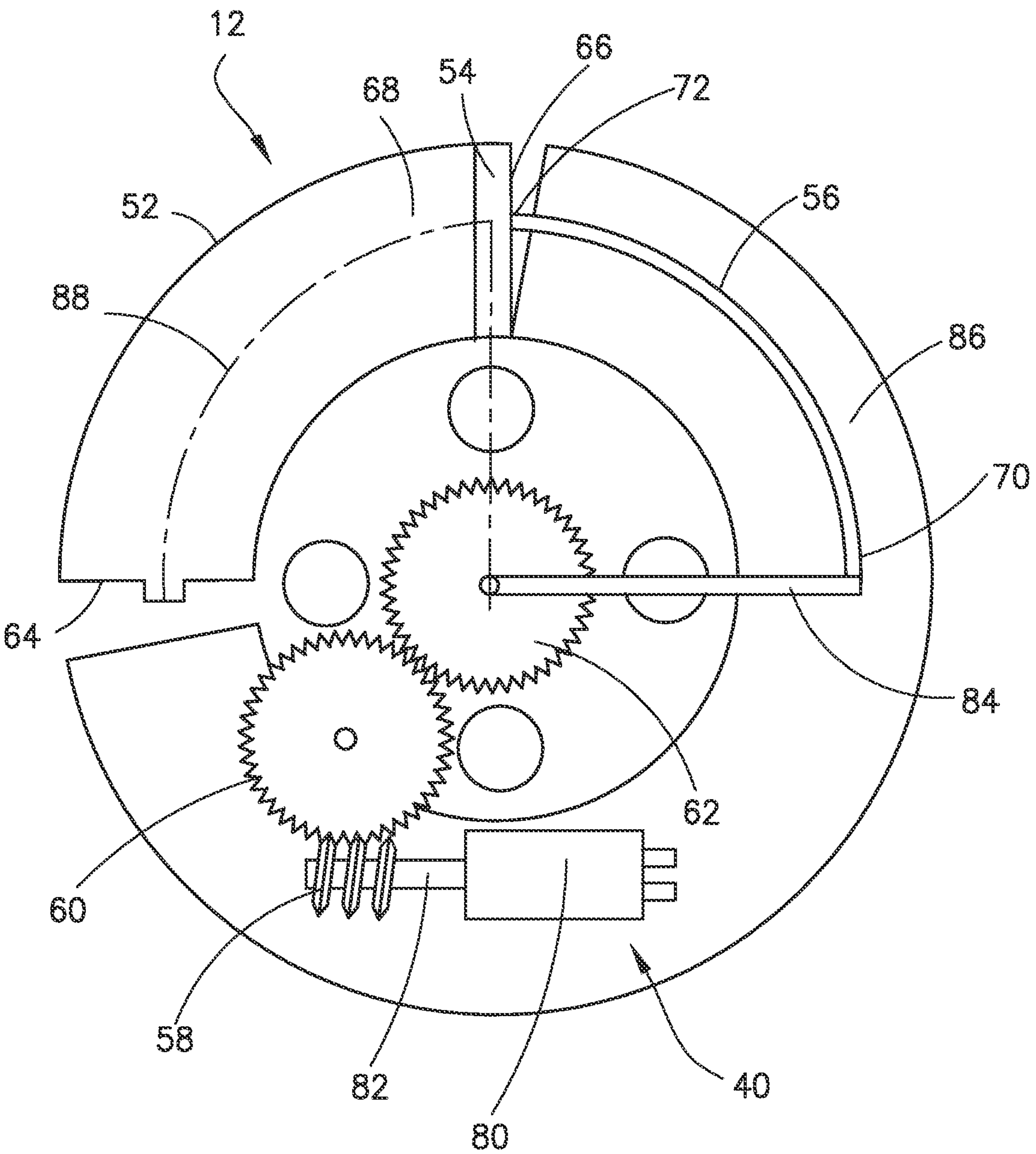
FIG. 2 is a schematic view of a reservoir and drive assembly of the drug delivery device of FIG. 1 according to one aspect or embodiment of the present application.

Referring to FIG. 2, in one aspect or embodiment, the reservoir 12 and the drive assembly 40 of the medical injector 10 includes a curved barrel 52, a stopper 54, a curved plunger rod 56, and at least one actuator, such as gear 58, 60, 62. The curved barrel 52 has a first end 64 and a second end 66 positioned opposite the first end 64, with the curved barrel 52 defining an interior space 68 configured to receive a fluid. The stopper 54 is received within the interior space 68, with the stopper 54 configured to move within the curved barrel 52 to dispense fluid from the curved barrel 52. The curved plunger rod 56 has a first end 70 and a second end 72 positioned opposite from the first end 70, with the curved plunger rod 56 connected to the stopper 54. The at least one gear 58, 60, 62 is configured to drive the curved plunger rod 56 and move the stopper 54 within the curved barrel 52. The curved plunger rod 56 length from the first end 70 to the second end 72 may be equal to or greater than a length of the curved barrel 52 from the first end 64 to the second end 66 plus the thickness of the stopper 54 such that the entire contents of the curved barrel 52 can be dispensed.

The curved plunger rod 56 and the stopper 54 may be formed integrally or may be formed separately, with the curved plunger rod 56 connected to the stopper 54 via any suitable connection arrangement. The curved barrel 52 is curved along an entire length extending from the first end 64 of the curved barrel 52 to the second end 66 of the curved barrel 52, although other suitable arrangements may be utilized. The curved plunger rod 56 is curved along an entire length extending from the first end 70 of the curved plunger rod 56 to the second end 72 of the curved plunger rod 56, although other suitable arrangements may be utilized. The drive assembly 40 further includes electric motor 80 configured to drive the at least one gear 58, 60, 62. In one aspect or embodiment, the at least one gear 58, 60, 62 includes a worm gear 58, a pinion gear 60, and a planetary gear set 62. The electric motor 80 includes a drive shaft 82, with the worm gear 58 secured to the drive shaft 82, the pinion gear 60 engaged with the worm gear 58 and the planetary gear set 62. A drive arm 84 connected to the planetary gear set 62 is connected to the curved plunger rod 56. Accordingly, upon actuation of the electric motor 80, the drive shaft 82 turns the worm gear 58, which rotates the pinion gear 60 and the planetary gear set 62 thereby rotating the drive arm 84. Rotating of the drive arm 84 moves the curved plunger rod 56, which, in turn, moves the stopper 54 within the curved barrel 52 to dispense fluid from the curved barrel 52 to the cannula 48 or other arrangement. In one aspect or embodiment, the curved plunger rod 56 includes a plurality of gear teeth along its length (not shown), which engages one or more gears driven by the electric motor 80. The curved barrel 52 may be used to infuse or deliver fluids using a gearing mechanism with rate adjustment using an active actuator or could be powered by a passive system for bolus or basal deliveries.

Referring again to FIG. 2, in one aspect or embodiment, the medical injector 10 includes a C-shaped printed circuit board assembly 86. The curved barrel 52 has a circular cross-section along a direction extending perpendicular to a curved central axis 88 extending from the first end 64 to the second end 66 of the curved barrel 52.

The curved barrel 52 and/or the curved plunger rod 56 conserves space and allows the overall size of the medical injector 10 to be minimized while still holding a sufficient volume of fluid. The curved barrel 52 and/or the curved plunger rod 56 also conserves the motion required to dispense fluid from medical injector 10 while enabling the use of gearing mechanisms with high efficiency. The curved barrel 52 allows the reservoir 12 to have a large arc length while keeping overall length less than the axis length, which allows the reservoir 12 to have a relatively small cross-sectional area thereby advantageously reducing surface friction and force needed to drive against back-pressure during delivery of the medicament.

In one aspect or embodiment, the cross-section of the curved barrel 52 is circular, elliptical, or other closed loop structure. In one aspect or embodiment, the stopper 54 is pushed and/or pulled using an internal structure, such as cables or rods. The height and cross-section of the curved barrel 52 can be varied for different volumetric infusion targets for various products. In one aspect or embodiment, the interior space 68 of the curved barrel 52 has a volume of 3-10 mL. In a further aspect or embodiment, the interior space 68 of the curved barrel 52 has a volume of 10-50 mL.

Figures 3, 4:
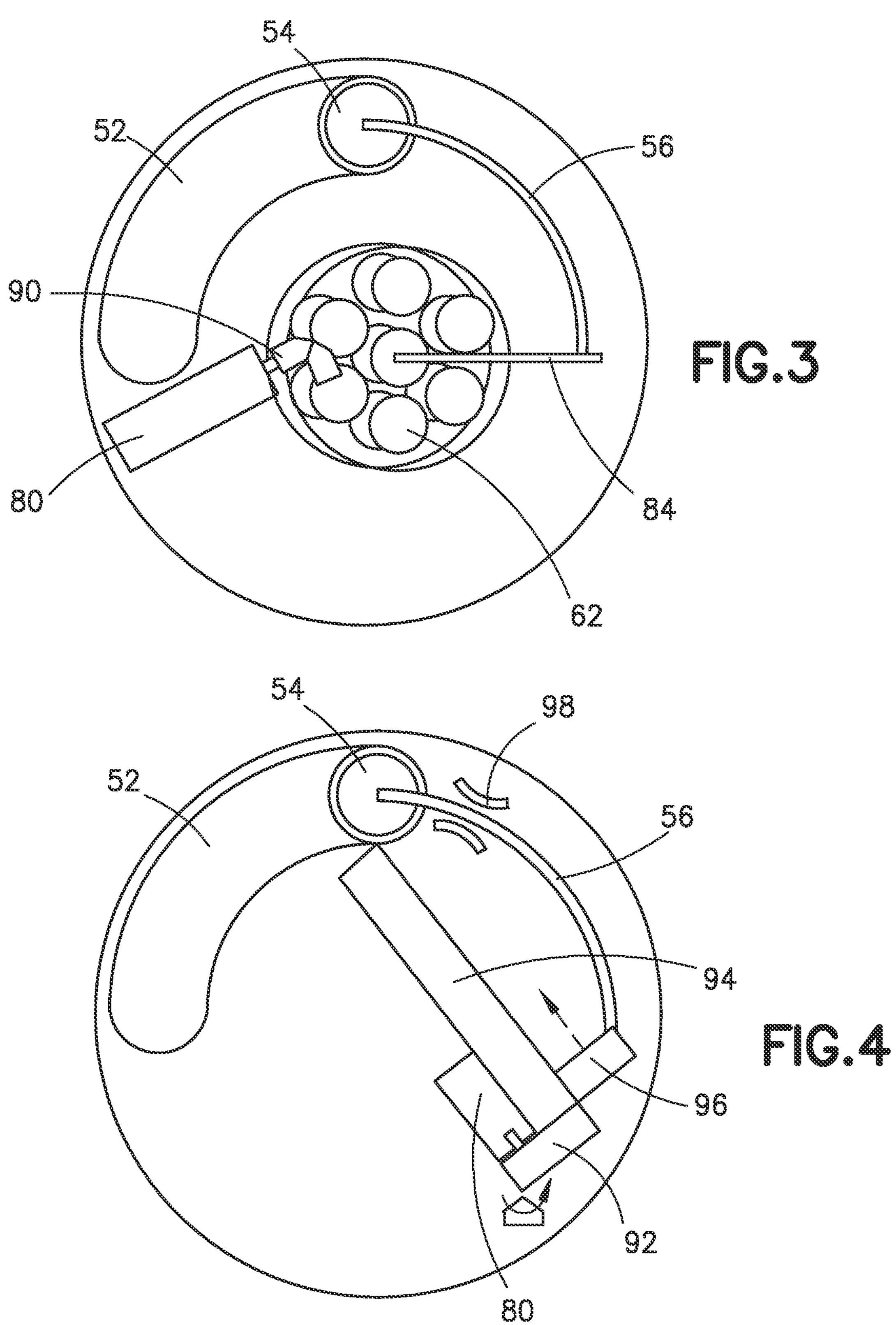
FIG. 3 is a schematic view of a reservoir and drive assembly of the drug delivery device of FIG. 1 according to a further aspect or embodiment of the present application.
FIG. 4 is a schematic view of a reservoir and drive assembly of the drug delivery device of FIG. 1 according to a further aspect or embodiment of the present application.

Referring to FIG. 3, in a further aspect or embodiment, the electric motor 80 is connected to a bevel gear 90, which rotates a gear of the planetary gear set 62 with the planetary gear set 62 turning the drive arm 84 to displace the curved plunger rod 56.

Referring to FIG. 4, in a further aspect or embodiment, the drive assembly 40 of the medical injector 10 includes a gearbox 92 connected to the electric motor 80, with the gearbox 92 rotating a leadscrew 94, which, in turn, translates a slider nut 96. The slider nut 96 moves the curved plunger rod 56, with a rack support bar 98 guiding and/or aligning the movement of the curved plunger rod 56.

Figures 5, 6:
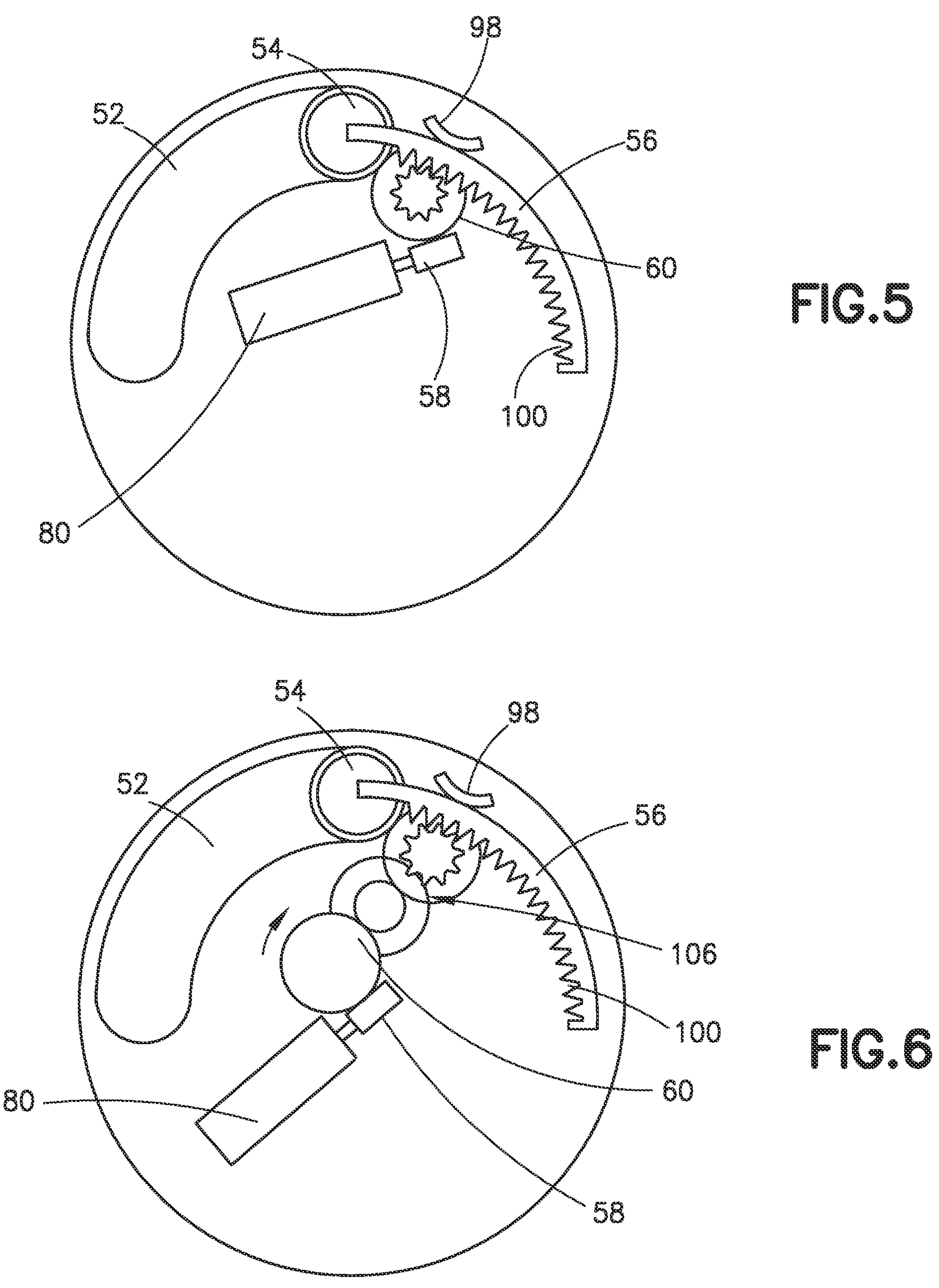
FIG. 5 is a schematic view of a reservoir and drive assembly of the drug delivery device of FIG. 1 according to a further aspect or embodiment of the present application.
FIG. 6 is a schematic view of a reservoir and drive assembly of the drug delivery device of FIG. 1 according to a further aspect or embodiment of the present application.

Referring to FIG. 5, in a further aspect or embodiment, the electric motor 80 is connected to the worm gear 58, which, in turn, rotates the pinion gear 60. The pinion gear 60 is engaged with a rack 100 positioned on the curved plunger rod 56, which moves the curved plunger rod 56, with the rack support bar 98 guiding and/or aligning the movement of the curved plunger rod 56. The rack 100 may be formed integrally with the curved plunger rod 56.

Referring to FIG. 6, in a further aspect or embodiment, the drive assembly 40 may be similar to the one shown in FIG. 5, except a spur gear set 102 is positioned between the worm gear 58 and the pinion gear 60.

Figures 7, 8:
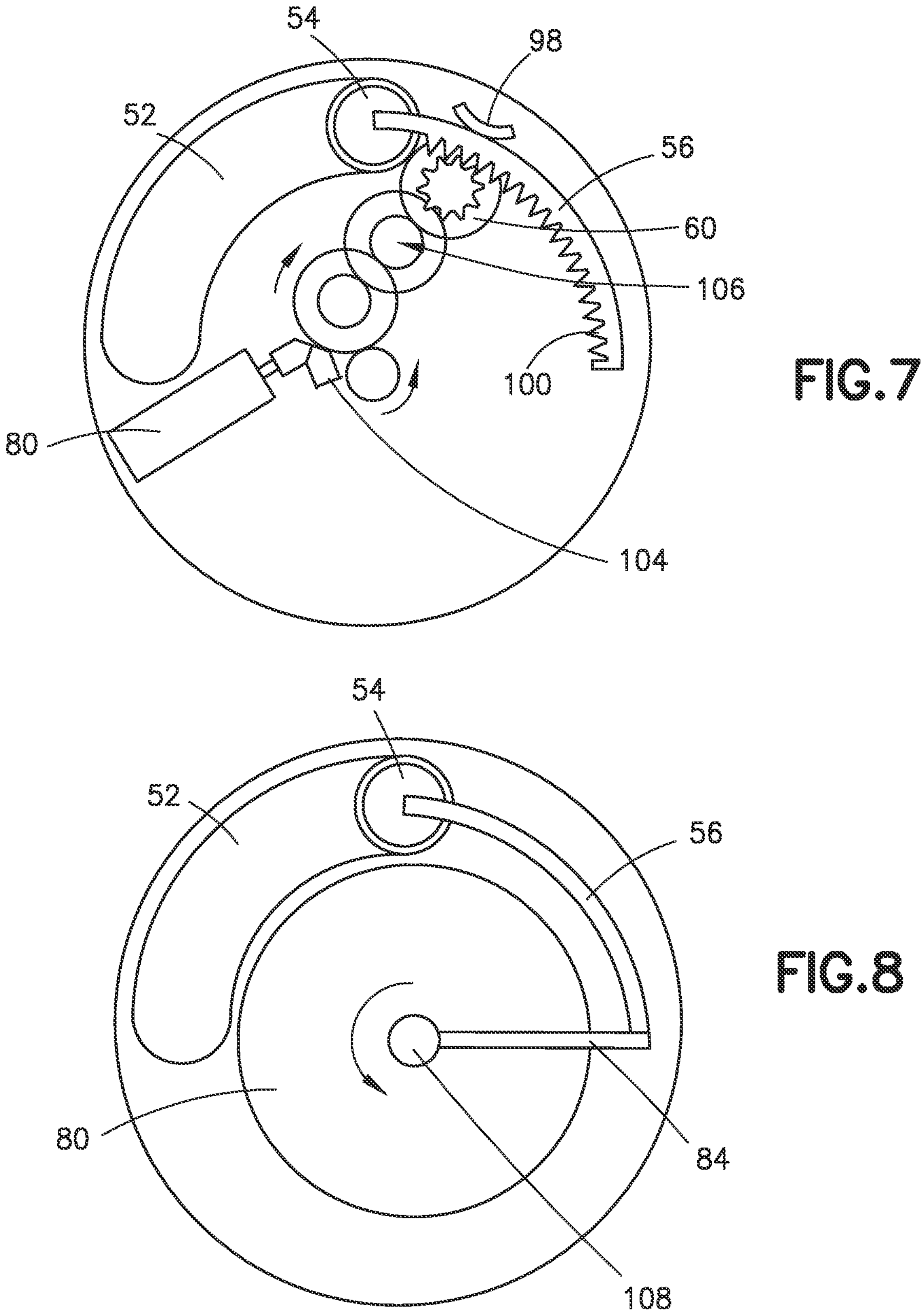
FIG. 7 is a schematic view of a reservoir and drive assembly of the drug delivery device of FIG. 1 according to a further aspect or embodiment of the present application.
FIG. 8 is a schematic view of a reservoir and drive assembly of the drug delivery device of FIG. 1 according to a further aspect or embodiment of the present application.

Referring to FIG. 7, in a further aspect or embodiment, the drive assembly 40 of the medical injector 10 includes a bevel gear 104 connected to the electric motor 80, with the bevel gear 104 rotating a spur gear set 106. A gear of the spur gear set 106 engages the pinion gear 60, which engages the rack 100 of the curved plunger rod 56.

Referring to FIG. 8, in a further aspect or embodiment, the electric motor 80 of the drive assembly 40 of the medical injector 10 is directly connected to the drive arm 84, which moves the curved plunger rod 56. The electric motor 80 may be a pancake-style electric motor. A revolute joint 108 may be positioned between the motor 80 and the drive arm 84.

Figure 9:
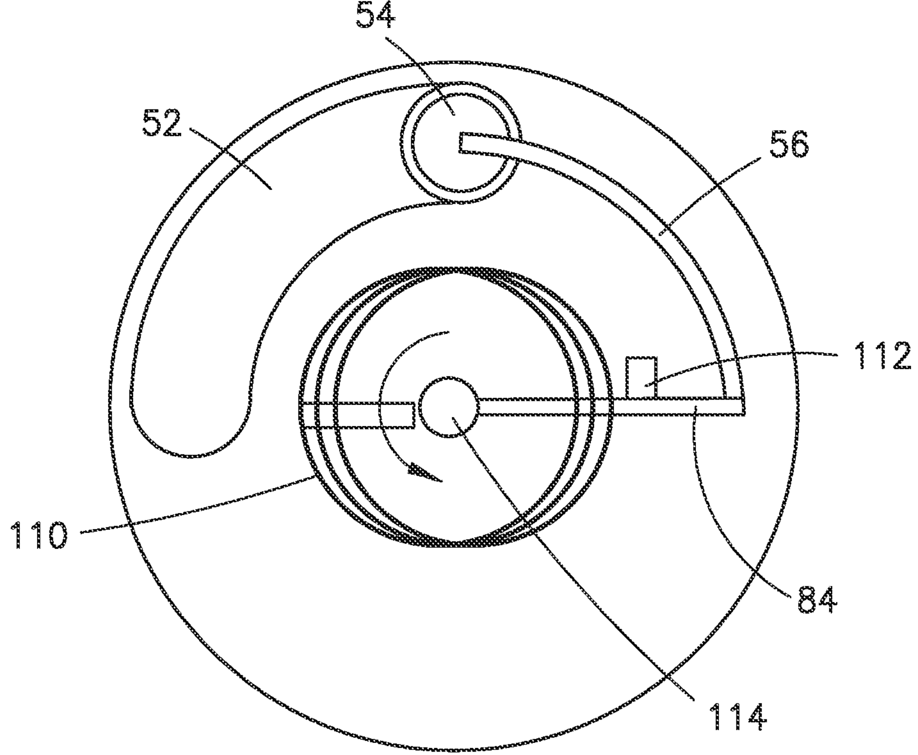
FIG. 9 is a schematic view of a reservoir and drive assembly of the drug delivery device of FIG. 1 according to a further aspect or embodiment of the present application.

Referring to FIG. 9, in a further aspect or embodiment, the drive assembly 40 of the medical injector 10 includes a wound rotational spring 110 retained by a pin 112. Removal of the pin 112, either manually by a patient or automatically by the medical injector 10, releases the spring 110 and biases the drive arm 84 to move the curved plunger rod 56. One end of the spring 110 is secured to the structure of the medical injector 10 and the moving end of the spring 110 is secured to the drive arm 84. The drive arm 84 is secured to the medical injector 10 via a pivot 114, such as a revolute joint.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A reservoir and drive assembly for a medical injector comprising:
- a curved barrel having a first end and a second end positioned opposite the first end, the curved barrel defining an interior space configured to receive a fluid;
- a stopper received within the interior space, the stopper configured to move within the curved barrel to dispense fluid from the curved barrel;
- a curved plunger rod having a first end and a second end positioned opposite from the first end, the curved plunger rod connected to the stopper;
- at least one actuator inducing movement of the stopper within the curved barrel; and
- an electric motor comprising a drive shaft, the electric motor configured to drive the at least one actuator, the at least one actuator comprising:
  - a worm gear;
  - a pinion gear; and
  - a planetary gear set, the worm gear is secured to the drive shaft and the pinion gear is engaged with the worm gear and the planetary gear set, and a drive arm is connected to the planetary gear set,
  - wherein the drive arm is connected to the curved plunger rod.

2. The reservoir and drive assembly of claim 1, wherein the curved plunger rod and at least a portion of the stopper are formed integrally.

3. The reservoir and drive assembly of claim 1, wherein the curved barrel is curved along an entire length extending from the first end of the curved barrel to the second end of the curved barrel.

4. The reservoir and drive assembly of claim 1, wherein the curved plunger rod is curved along an entire length extending from the first end of the curved plunger rod to the second end of the curved plunger rod.

5. The reservoir and drive assembly of claim 1, further comprising a printed circuit board assembly, wherein the printed circuit board assembly is C-shaped.

6. The reservoir and drive assembly of claim 1, wherein the curved barrel has a circular cross-section along a direction extending perpendicular to a curved central axis extending from the first end to the second end of the curved barrel.

7. A medical injector comprising:
- a curved barrel having a first end and a second end positioned opposite the first end, the curved barrel defining an interior space configured to receive a fluid;

a stopper received within the interior space, the stopper configured to move within the curved barrel to dispense fluid from the curved barrel;

a curved plunger rod having a first end and a second end positioned opposite from the first end, the curved plunger rod connected to the stopper;

at least one actuator inducing movement of the stopper within the curved barrel;

a power source;

a cannula configured to be inserted into a skin of a patient; and an electric motor comprising a drive shaft, the electric motor configured to drive the at least one actuator, the at least one actuator comprising:

a worm gear;

a pinion gear; and a planetary gear set, the worm gear is secured to the drive shaft and the pinion gear is engaged with the worm gear and the planetary gear set, and a drive arm is connected to the planetary gear set, wherein the drive arm is connected to the curved plunger rod.

8. The medical injector of claim 7, wherein the curved plunger rod and at least a portion of the stopper are formed integrally.

9. The medical injector of claim 7, wherein the curved barrel is curved along an entire length extending from the first end of the curved barrel to the second end of the curved barrel.

10. The medical injector of claim 7, wherein the curved plunger rod is curved along an entire length extending from the first end of the curved plunger rod to the second end of the curved plunger rod.

* * * * *